United States Patent [19]

Shah et al.

[11] Patent Number: 4,900,662

[45] Date of Patent: Feb. 13, 1990

[54] CK-MM MYOCARDIAL INFARCTION IMMUNOASSAY

[75] Inventors: Vipin D. Shah, Saratoga; Shing-Erh Yen, Foster City; Gerald M. Anchin, Santa Cruz, all of Calif.

[73] Assignee: International Immunoassay Laboratories, Inc., Santa Clara, Calif.

[21] Appl. No.: 76,038

[22] Filed: Jul. 21, 1987

[51] Int. Cl.$^4$ .................. G01N 33/00; G01N 33/53
[52] U.S. Cl. .......................... 435/7; 436/524; 436/528; 436/538; 436/547; 436/548; 436/811; 436/815; 530/387; 530/388; 935/110
[58] Field of Search ............... 435/7, 172.2; 436/524, 436/528, 531, 538, 547, 548, 811, 815; 530/387, 388; 935/110

[56] References Cited

U.S. PATENT DOCUMENTS

| | | | |
|---|---|---|---|
| 4,237,219 | 12/1980 | Roberts | 436/804 X |
| 4,260,678 | 4/1981 | Lepp et al. | 436/805 X |
| 4,353,982 | 10/1982 | Gomez et al. | 436/811 X |
| 4,624,916 | 11/1986 | Shah et al. | 436/527 X |

OTHER PUBLICATIONS

Grace, A. M. et al, "Sensitive Quantification of Isoforms of Canine MM Creatine Kinase", Anal. Biochem. 149, 209–217 (1985).
Morison et al, Clin. Chem. 34: 535–538 (1988).

Primary Examiner—Robert J. Warden
Assistant Examiner—Richard Wagner
Attorney, Agent, or Firm—William B. Walker; Laura Terlizzi

[57] ABSTRACT

Methods and reagents for early detection of myocardial infarction determine the level of CK-MM$_A$ and the level of the combined CK-MM$_A$ and CK-MM$_B$ in a serum sample. From these measurements, the time of the acute phase can be more accurately determined. Novel anti-(CK-MM$_A$) antibodies, anti-(CK-MM$_B$) antibodies, anti-(CK-MM$_{(A+B)}$) antibodies, labeled and insolubilized derivatives of these antibodies, labeled CK-MM isoforms, and kits containing one or more of these reagents are also described.

26 Claims, No Drawings

CK-MM MYOCARDIAL INFARCTION IMMUNOASSAY

FIELD OF THE INVENTION

This invention relates to the measurement of biological markers which are released into body fluids at the onset of acute diseases for diagnostic purposes. In particular, this invention relates to the measurement of CK-MM isoforms in patient serum for purposes of diagnosis of myocardial infarction or other acute injuries which cause the release of CK-MM isoforms into the blood stream.

BACKGROUND OF THE INVENTION

Diagnosis of acute disease is often based on abnormal levels of disease markers such as enzymes and hormones in biological fluids such as serum, particularly when they change momentarily during the acute phase of disease.

The biological activity and physical properties of proteins such as enzymes and hormones is determined by structural features of the molecule, and these features are often modified by endogenous conversions factors present in body fluids. Such conversion may cause the loss of biological activity or change in physical properties such as electrophoretic mobility of the molecule. The conversion products may coexist with the original molecule immediately following the onset of an acute disease, but with the passage of time, one may find only the altered protein in the body fluids.

Many tests have been developed which measure the native form of a protein marker in a body fluid. Bioassay techniques have been traditionally used to measure enzyme activity, and when the altered form of the enzyme marker is inactive, the enzyme activity is an adequate measurement of the enzyme level in the system. Immunoassays, while offering a more convenient approach, is dependent upon having antibodies which bind selectively with the moiety to be measured. When the altered protein product differs only slightly from a native marker protein, antibodies may be unable to distinguish and will react with both moieties, giving an erroneous result. Thus the primary immunoassay efforts have addressed development of antibodies which bind specifically with the native protein marker, antibodies binding with the altered forms generally being avoided.

This invention relates to the measurement of an analyte pair consisting of the native protein and an initial, altered form and of the native protein, both measured values being useful for diagnosis. The analyte pair level remains elevated longer than the native protein, and the ratio of the amount of native analyte to the analyte pair provides a basis for more accurately estimating the time elapsed since the onset of the acute episode. In one application of this invention for the diagnosis of myocardial infarction, CK-MM isoforms are measured.

The enzyme creatine kinease (CK, ATP:creatine N-phosphotransferase) catalyzes the reversible transfer of phosphate group from ATP to creatine. It exists in the cytoplasm of the cells of human tissue as a dimer composed of two subunits commonly identified as the M-subunit and the B-subunit. Three of the commonly found isoenzymes of CK comprises combinations of these subunits and are correspondingly identified as CK-MM, CK-MB and CK-BB. Abnormality of these isoenzymes in body fluids generally suggest acute disease. CK-MB is associated with acute myocardial infarction, for example. Appearance of CK-MB isoenzymes in serum is indicative of myocardial infarction. CK-BB isoenzyme appearance in serum is indicative of brain injury and other abnormalities. CK-MM isoenzymes are present in the serum of normal patients.

Proteins such as CK-MM and CK-MB are labile and have short lives in living systems. Other endogenous enzymes act on isoenzymes and isoforms and alter their molecular size and structure. Such alteration may affect the catalytic activity, immunoreactivity and other properties. They may loose their catalytic activity and still retain immunoreactivity. They may migrate differently in separation procedures and appear in unexpected fractions. The apparent results of immunological techniques may not agree with those obtained with non-immunological techniques because of the lack of binding specificity of the antibodies. CK-BB is also believed to produce yield altered forms, but due to its short half-life and lability, no altered forms have yet been observed.

Antibodies produced with CK isoforms are frequently cross-reactive. Antibodies have been produced with CK-BB which react with CK-MB (CK-B antibodies) as reported by Shell, W. et al, "Radioimmunoassay of creatine kinease." CLINICAL NUCLEAR CARDIOLOGY. New York: Grune & Stratton pp 462–478 (1981), and antibodies have been produced with CK-MM which react with CK-MB (CK-M antibodies) as reported by Wicks, R. et al, Clin.Chem. 28:54–58 (1982). That the antibodies appear to bind with the altered proteins is also observed. Shell, W. et al, SYLLABUS. Clinical Radioassay Society, 9th Annual Meeting, p 61 (1981) speculates that an immunoassay for the CK-Bi inactive product of CK-B protein might show that the inactive form of CK-BB was present in a major proportion in serum, no CK-Bi selectively binding antibody has been reported.

DESCRIPTION OF THE PRIOR ART

Creatine kinase isoenzymes CK-MM has been further resolved into at least three (CK-MM$_A$, CK-MM$_B$, CK-MM$_C$) enzymatically active isoforms, and CK-MB has been further resolved into two enzymatically active isoforms (CK-MB$_A$, CK-MB$_B$) by electrophoresis as reported by Weaver, R. et al, Clin.Chem.Acta. 75:377 (1977); Chapelle et al, Clin.Chem. 26:457–462 (1980); Yasmineh, W. et al, J.Lab.Clin.Med. 98:109–118 (1981); Falter, H. et al, Clin.Biochem. 14:3–7 (1981); and George, S. et al, J.Biol.Chem. 259:2667–2674 (1984); and Panteghini, M. et al, Clin.Chem.Acta. 155:1–10 (1986). The serum concentrations of the CK-MM isoforms versus time following a myocardial infarction have been studied by Morelli, R. et al, Circulation. 67(6):1283–1289 (1983); Hashimoto, H. et al, Circulation. 71(2):363–369 (1985); Jaffe et al, Circulation. 74(1):105–109 (1986); and Wu, A. et al, Clin.Chem. 33(3):358–362 (1987), and several of these authors suggested that the analysis of CK-MM subtypes could be useful in the early diagnosis of AMI, even though CK-MM isoenzyme exists in the serum of patients who are not suffering from acute myocardial infarction.

At the onset of acute myocardial infarction (AMI), several isoenzymes of CK are released from damaged myocardium along with transaminase and myoglobin, and enter the circulating blood. The amounts of CK-MB and CK-MM are known to increase in circulation after the onset of AMI. With some exceptions, the levels of both CK-MM and CK-MB become abnormal within 3-6 hours after the onset of AMI. Other markers released by AMI are myoglobin and myosin light chains. These later markers offer some advantage over CK-MB measurements because the CK-MB does not peak until 18-24 hours after the onset of chest pain, in the absence of thrombolytic agent treatment.

CK-MM$_A$, the isoform of CK-MM present in a tissue such as myocardium tissue, is a homodimer of two M chains, each with a terminal lysine group (Jaffe, A. et al, supra). After release of CK-MM$_A$ into plasma, the terminal lysine group from one chain is rapidly removed by a yet to be identified conversion factor such as a carboxypeptidase, yielding CK-MM$_B$, an isoform with a terminal lysine group on one chain. Subsequent cleavage of the other terminal lysine group yields a third isoform, CK-MM$_C$, the major ultimate form.

Several conflicting nomenclatures have been used to designate the various isoforms of CK-MM, and the nomenclature used in this patent is that suggested by Jaffe et al (supra). Morelli et al (supra) and Jaffe et al (supra) have shown that the ratio of CK-MM$_A$/CK-MM$_C$ increases following AMI and can be used as an early indicator of AMI. The analytical development in this field has focused on the adaptation of various analytical techniques to the measurement of the CK-MM$_A$/CK-MM$_C$ ratio, and the use of this ratio in the early diagnosis of AMI.

Koch et al, *Clin.Chem.* 32:186 (1986) reviews the application of electrophoresis, column chromatography, immunochemical and immunometric methods for measuring CK-MB. CK isoenzyme measurements have been made by electrophoretic separations on agarose and cellulose acetate; with electrophoretic separation wit fluorescent visualization and electrophoretic separation with elution of either the protein or substrate from the media (Roberts, R. et al, *Am.J.Cardiol.* 33:650-654 (1974)); by ion exchange column separation with spectrophotometric analysis of activity (Mercer, D. et al, *Clin.Chem.* 20:36-40 (1974); by kinetic differentiation of isoenzymes (Witteveen, S. et al, *Proc.Natl..Acad.Sci.U.S.A.* 71:1384-1387 (1974); by selective activation of proteins (Rao, P. et al, *Clin.Chem.* 21:1612-1618 (1975); radioimmunoassays for determination of CK-BB and CK-MB levels using antibodies which are not cross-reactive with CK-MM (Roberts, R. et al, *Science.* 194:855-857 (1976), and U.S. Pat. Nos. 4,237,219 and 4,267,271); and immunoinhibition using antisera against CK-MM and CK-BB isoenzymes which were not completely cross-reactive with CK-MB (Jockers-Wretou et al, *Clin.Chim.Acta.* 58:223-232 (1975).

U.S. Pat. No. 3,932,221 describes use of immunoprecipitation procedures for determining isoenzyme levels in body tissues or fluids using isoenzyme-antibody complexes and lists most types of body enzymes including creatine kinase as a suitable object for this approach. No CK-binding antibodies are disclosed in the patent.

U.S. Pat. No. 3,994,783 discloses a differential assay for CK isoenzymes involving a measurement of total CK enzyme activity before and after CK-MB activation.

U.S. Pat. No. 4,012,285 discloses a differential assay for isoenzymes comprising precipitating specific isoenzymes from solution with specifically binding antibodies, and measuring the enzymatic activity of the unbound enzymes remaining in the solution. Although CK enzymes are included in a listing of suitable isoenzyme systems for this method, no CK-binding antibodies are disclosed.

U.S. Pat. No. 4,067,775 discloses a method for determining CK-MB activity in a body fluid by inactivating the CK-M subunit with a anti-M antibody, and measuring the remaining activity remaining, attributable to the CK-B subunit. U.S. Pat. Nos. 4,237,219 and 4,267,271 disclose radioimmunoassays for determination of CK-BB and CK-MB levels using antibodies which bind with the CK-B monomer, react with CK-BB and cross-react with CK-MB, but which are not cross-reactive with CK-MM. U.S. Pat. No. 4,353,982 discloses an immunochemical approach to measuring CK-MB antibody by binding one of the CK-B or CK-M subunits with an specifically binding first antibody, binding the first antibody with a specific immunoprecipitation, and binding the other of the CK-B or CK-M subunits with a labeled specifically binding third antibody. U.S. Pat. No. 4,298,592 describes a double antibody competition radioimmunoassay method using $^{125}$I labeled CK-BB solution. Sandwich techniques are disclosed in U.S. Pat. No. 4,624,916 and Canadian Pat. No. 1,172,958.

U.S. Pat. No. 4,105,499 describes column chromatographic separation of CK MB for serum for rapid detection of heart attack, and U.S. Pat. No. 4,046,634 discloses separation of CK isoenzymes by ion exchange chromatography. U.S. Pat. No. 4,260,678 describes an affinity column procedure for determining creatine kinase enzymes in serum using immobilized antibodies specific for CK-MM or CK-BB, and testing the immobilized enzyme for activity.

SUMMARY AND OBJECTS OF THE INVENTION

This invention is a method for determining the initial elevated concentration level of CK-MM$_A$ in patient serum following a myocardial infarction comprising determining the combined concentration of CK-MM$_A$ and CK-MM$_B$ and the concentration of CK-MM$_A$ in patient serum.

One aspect of the method of this invention comprises determining the level of CK-MM$_A$ in a serum sample comprising interacting CK-MM$_A$ with anti-(CK-MM$_A$) antibody, and determining the CK-MM$_A$ bound with anti-(CK-MM$_A$) antibody. The anti-(CK-MM$_A$) antibody can be bound to an insoluble support, the insoluble support contacted with the serum sample for a time sufficient to permit CK-MM$_A$ conjugation with anti-(CK-MM$_A$) antibody, and the amount of CK-MM$_A$ bound to the insoluble support determined. Alternatively, an anti-(CK-MM) antibody can be bound to an insoluble support, the insoluble support contacted with the serum sample for a time sufficient to permit CK-MM$_A$ conjugation with the anti-(CK-MM) antibody, contacting the insoluble support with anti-(CK-MM$_A$) antibody, and determining the amount of anti-(CK-MM$_A$) antibody bound to the insoluble support. As a further embodiment, CK-MM$_A$ is bound to an insoluble support, the insoluble support is contacted with a mixture of the serum sample and labeled anti-(CK-MM$_A$) antibody for a time sufficient to permit CK-MM$_A$ conjugation with the anti-(CK-MM$_A$) antibody, and the amount of the label on the insoluble support or remaining in the mixture is determined.

Another aspect of this invention comprises a method for determining the level of CK-MM$_B$ in a serum sample comprising interacting CK-MM$_B$ with anti-(CK-MM$_B$) antibody, and determining the CK-MM$_B$ bound with anti-(CK-MM$_B$) antibody. The anti-(CK-MM$_B$) antibody can be bound to an insoluble support, the insoluble support contacted with the serum sample for a time sufficient to permit CK-MM$_B$ conjugation with anti-(CK-MM$_B$) antibody, and the amount of CK-MM$_B$ bound to the insoluble support determined. Alternatively, an anti-(CK-MM) antibody is bound to an insoluble support, the insoluble support can be contacted with the serum sample for a time sufficient to permit CK-MM$_B$ conjugation with the anti-(CK-MM) antibody, contacting the insoluble support with anti-(CK-MM$_B$) antibody, and determining the amount of anti-(CK-MM$_B$) antibody bound to the insoluble support. In a further embodiment, CK-MM$_B$ is bound to an insoluble support, the insoluble support is contacted with a mixture of the serum sample and labeled MM$_B$ for a time sufficient to permit anti-(CK-MM$_B$) antibody conjugation with the anti-(CK-MM$_B$) antibody, and the amount of the label on the insoluble support or remaining in the mixture is determined.

In a still further aspect of the method of this invention, the level of CK-MM$_{(A+B)}$ in a serum sample is determined by interacting CK-MM$_{(A+B)}$ with anti-(CK-MM$_{(A+B)}$) antibody, and determining the CK-MM$_{(A+B)}$ bound with anti-(CK-MM$_{(A+B)}$) antibody. The anti-(CK-MM$_{(A+B)}$) antibody can be bound to an insoluble support, the insoluble support contacted with the serum sample for a time sufficient to permit CK-MM$_{(A+B)}$ conjugation with anti-(CK-MM$_{(A+B)}$) antibody, and the amount of CK-MM$_{(A+B)}$ bound to the insoluble support determined. Alternatively, an anti-(CK-MM) antibody is bound to an insoluble support, the insoluble support is contacted with the serum sample for a time sufficient to permit CK-MM$_{(A+B)}$ conjugation with the anti-(CK-MM) antibody, contacting the insoluble support with anti-(CK-MM$_{(A+B)}$) antibody, and determining the amount of anti-(CK-MM$_{(A+B)}$) antibody bound to the insoluble support. In a still further embodiment, CK-MM$_{(A+B)}$ is bound to an insoluble support, the insoluble support is contacted with a mixture of the serum sample and labeled MM$_{(A+B)}$ for a time sufficient to permit anti-(CK-MM$_{(A+B)}$) antibody conjugation with the anti-(CK-MM$_{(A+B)}$) antibody, and the amount of the label on the insoluble support or remaining in the mixture is determined.

In the preferred method, the level of CK-MM$_A$ and the combined levels of CK-MM$_A$ and CK-MM$_B$ are determined in the sample, the data providing a more accurate estimate of the time of the infarction.

Novel reagents of this invention include an anti-(CK-MM$_A$) antibody which does not bind significantly with CK-MB, CK-MM$_B$ or CK-MM$_C$; an anti-(CK-MM$_B$) antibody which does not bind significantly with CK-MB, CK-MM$_A$ or CK-MM$_C$; an anti-(CK-MM$_{(A+B)}$) antibody which binds with CK-MM$_A$ and CK-MM$_B$, but does not bind significantly with CK-MB, or CK-MM$_C$; labeled derivatives of these antibodies; insoluble supports to which these antibodies are adhered; and kits containing one or more of these antibodies or their derivatives.

DETAILED DESCRIPTION OF THE INVENTION

This invention relates to the measurement, in a liquid specimen of a patient suffering from an acute disease, of transiently elevated biologically active protein and an analyte pair consisting of said protein and its initial endogenously altered form. Specifically, the details are provided using CK-MM$_A$ as an example of transiently elevated protein and acute myocardial infarction as an example of acute disease. In general, the method of this invention involves making and the selection of antibodies which can be used for specific measurement of CK-MM$_A$ alone and for specific measurement of an analyte pair consisting of CK-MM$_A$ and its initially altered form, CK-MM$_B$.

The method of this invention is a test used for diagnosis and treatment based on the concurrent measurement of an analyte pair consisting of the native form and first altered form of a biologically active protein released during the acute phase of a disease. The amount of the analyte pair and the ratio of native protein to the analyte pair is used to estimate the time of the initiation of the acute disease, that is, the time the native protein is released into the blood stream and the formation of the altered form begins. In one specific aspect, the diagnosis of myocardial infarction is facilitated by the measurement of CK-MM$_A$ and the protein pair of CK-MM$_A$ and CK-MM$_B$ concurrently. From the levels measured, the time of the infarction can be more accurately estimated.

The methods of this invention use polyclonal and/or monoclonal antibodies in a novel immunoassay approach. The reagent antibodies and kits containing them are also aspects of this invention.

ANTIBODY REAGENTS

Novel antibody reagents of this invention are polyclonal and monoclonal antibodies of two binding types, one binding type which binds selectively with CK-MM$_A$ and another binding type which binds selectively with both CK-MM$_A$ and CK-MM$_B$ (hereinafter represented as CK-MM$_{(A+B)}$).

The term "antibody" as used herein is defined to include antibodies of classes IgG, IgM, IgA, IgD, and IgE, and fragments and hybrid derivatives of antibodies including Fab, and F(ab')$_2$ fragments of antibodies. The term anti-(CK-MM$_A$) antibody is defined herein to designate an antibody which binds selectively with CK-MM$_A$ and which does not bind in significant quantities with CK-MB, CK-MM$_B$ or CK-MM$_C$ isoforms. The term anti-(CK-MM$_{(A+B)}$) antibody is defined herein to designate an antibody which binds selectively with CK-MM$_A$ and CK-MM$_B$ and which does not bind in significant quantities with CK-MB or CK-MM$_C$ isoforms. The latter can comprise a mixture of anti-(CK-MM$_A$) antibodies and anti-(CK-MM$_B$) antibodies. If the antibody is a monoclonal antibody, it can be a novel monoclonal antibody of this invention which binds selectively with both K-MM$_A$ and CK-MM$_B$ but not with CK-MB or CK-MM$_C$.

The polyclonal antibodies can be prepared by conventional procedures, with any mammal used for polyclonal antibody production. Generally a rabbit, guinea pig or goat is adequate. In producing the antibody, a predetermined amount of CK-MM$_A$ obtained from total CK-MM heart extract according to the method of Vaidya et al, *Biochimica et Biophysica Acta.* 790:230–237 (1984) is diluted with a physiological saline solution in a suitable concentration. This diluted solution is further diluted by mixing it with a complete Freund's adjuvant to prepare an emulsion. The suspension is then administered to the mammal. For example, the suspension can be administered by intraperitoneal, intramuscular or subcutaneous routes to a rabbit in an amount of 0.05 to a maximum, non-lethal dose which might be as high as 5 mg of the antigen in every administration, and the administration can be continued every other week for 2 to 10 months. Blood is removed from the mammal when the antibody titer is sufficiently elevated, generally one to 2 weeks after the last challenge administration of the suspension. The blood taken from the animal is treated by centrifugal separation to separate the serum containing the antibody.

The polyclonal antibody serum is then affinity purified using conventional affinity chromatography techniques such as those described by Mishell and Shilgi in SELECTED METHODS IN CELLULAR IMMUNOLOGY. San Francisco: Freeman (1980), the entire contents of which are hereby incorporated by reference. Suitable absorbents for use in affinity chromatography include cross-linked agarose and cross-linked polyacrylamides to which the selected CK-MM binding antibody is covalently bonded. For removal of antibodies cross-reacting with CK-MB and CK-MM$_C$, the antibody serum is passed through columns to which are coupled these materials. A portion of the eluant containing the remaining antibody can then be passed through a CK-MM$_A$ and then through a CK-MM$_B$ column to yield antibodies, eluted from the CK-MM$_B$ column which bind specifically with CK-MM$_B$. Another portion of the eluant containing the remaining antibody can then be passed through a CK-MM$_B$ and then through a CK-MM$_A$ column to yield antibodies, eluted from the CK-MM$_A$ column which bind specifically with CK-MM$_A$. Repetition of the column separation procedures may be required to effect the desired separations.

In these procedures, the antibody solution can be applied to the column in a phosphate buffered saline solution, and the antibodies can be eluted with a 2.5M NaSCN solution, pH 8.0. Antibody concentration, if desired, can be achieved by negative pressure dialysis or ultrafiltration. The antibody solution is stable at temperature of 4° C. or less.

Monoclonal antibodies of this invention made from the CK-MM$_A$, purified as described above, are prepared by conventional procedures, generally following the method of Kohler and Milstein, Nature. 256:495–497 (1975). More recent developments are reviewed in Goding, J.W. MONOCLONAL ANTIBODIES: PRINCIPLES AND PRACTICE. New York: Academic Press (1983) and the references cited therein, the entire contents of which are hereby incorporated by reference.

The hybridoma is prepared by immunizing mice or rats with the CK-MM$_A$. While female A/J mice (H-2a haplotype, Jackson Laboratories, Bar Harbor, ME) are preferred, it is contemplated that other mice or rat strains can be used. The immunization schedule and concentration of antigen in the suspension should be such as to produce useful quantities of suitably primed splenocytes and/or lymphocytes.

The suspended spleen cells are fused with mouse or rat myeloma cells from a suitable cell line by the use of a suitable fusion promoter. This can be either Sendai Virus, polyethylene glycol or an electrical field. Many mouse myeloma cell lines are known and available, generally from members of the academic community and various deposit banks such as the American Type Culture Collection, Rockville, Md. Balb/C myeloma cells lines are preferred. The myeloma cell line used should preferably be medium sensitive so that unfused myeloma cells will not survive in a selective medium, while hybrids will survive. The most common class is 8-azaguanine resistant cell lines, which lack the enzyme hypoxanthine guanine phosphoribosyl transferase and hence will not be supported by HAT (hypoxanthine, aminopterin, and thymidine) medium. It is also generally preferred that the myeloma cell line used be of the so-called "non-secreting" type, in that it does not produce any antibody, although secreting types may be used. While the preferred fusion promoter is polyethylene glycol having an average molecular weight from about 1000 to 4000 (commercially available as PEG 1000, etc.), other fusion promoters known in the art can be used.

The supernatant in each container (well) containing a hybridoma is then examined for the presence of antibody which binds selectively with CK-MM$_A$ or selectively with CK-MM$_{(A+B)}$ proteins and which does not bind to CK-MB or CK-MM$_C$ isoforms. Procedures suitable for screening are described by Goding, J. W. (supra, pp 72-84). One particular suitable method involves a competition between an anti-mouse immunoglobulin bound to an insoluble support such as a microtiter tray well and a mixture of labeled CK-MM$_A$ and culture supernatant or between an insolubilized anti-mouse immunoglobulin and a mixture of labeled CK-MM$_C$ and culture supernatant, the amount of label bound to the insoluble support being read to determine the binding of supernatant with the antibodies in the culture supernatant. Another suitable procedure comprises the application of the culture supernatant in a dot to a layer of nitrocellulose gel to which the selected isoform is adhered, rinsing the gel layer, contacting the gel layer with a chromogen labeled antibody or fluorescent labeled antibody which will bind to the Fc portion of any antibodies bound to gel layer, rinsing the gel layer to remove unbound labeled antibody, and examining the gel layer to determine if bound chromogen or fluorogen is evident where the dot was applied. Automatic tray readers can be used to quickly identify the wells having hybridomas yielding antibodies which bind to the proteins adhered to the insoluble surface.

After the desired hybridomas have been selected and cloned, the resultant antibody can be produced by in vitro culturing in a suitable medium followed by recovery of the antibody from the supernatant. Alternatively, the hybridoma can be injected into mice, preferably syngenic or semisyngenic mice. The hybridoma will cause formation of antibody producing tumors after a suitable incubation time. These will produce a high concentration of the desired antibody (about 5–20 mg/ml) in the bloodstream and peritoneal exudate (ascites) of the host mouse. Although the host mice will also have normal antibodies in their blood and ascites, the concentration of the normal antibodies will be only about 5 percent of the concentration of the desired monoclonal antibody.

In several embodiments of the diagnostic method of this invention, a labeled antibody reagent is used. The antibody reagent is labeled, i.e., chemically bond to a distinctive moiety which can be observed or measured to verify or quantify the presence of the antibody in a solution or on a solid surface. Ligands and groups which can be conjugated to the antibodies of this invention for use in diagnostic procedures include elements, compounds or biological materials which have physical or chemical characteristics which can be used to distinguish the antibodies to which they are bonded from other antibodies.

The specific activity of the radiolabels used with radiolabeled antibodies of this invention antibody depends upon the half-life, isotopic purity of the radioactive label and how the label is incorporated into the antibody. Table A lists several commonly used isotopes, their specific activities and half-lives. In immunoassay tests, the higher the specific activity, in general, the better the sensitivity.

TABLE A

| Isotope | Specific Activity of Pure Isotope (Curies/mole) | Half-Life |
|---|---|---|
| $^{14}C$ | $6.25 \times 10^1$ | 5720 years |
| $^{3}H$ | $2.91 \times 10^4$ | 12.5 years |
| $^{35}S$ | $1.5 \times 10^6$ | 87 days |
| $^{125}I$ | $2.18 \times 10^6$ | 60 days |
| $^{32}P$ | $3.16 \times 10^6$ | 14.3 days |
| $^{131}I$ | $1.62 \times 10^7$ | 8.1 days |

Procedures for labeling antibodies with radioactive isotopes listed in Table A are generally known in the art. Tritium labeling procedures are described in U.S. Pat. No. 4,302,438, for example. Iodinating, tritium labeling and $^{35}S$ labeling procedures especially adapted for murine monoclonal antibodies are described by Goding, J. W. MONOCLONAL ANTIBODIES: PRINCIPLES AND PRACTICE. New York: Academic Press pp 124–126 (1983) and the references cited therein. Other procedures for iodinating antibodies are described by Hunter and Greenwood, *Nature*. 144:945 (1962) and David et al, *Biochemistry*. 13:1014–1021 (1974) and in U.S. Pat. Nos. 3,867,517 and 4,376,110.

Antibodies labeled with enzymes are particularly useful. Suitable examples of enzyme labeling of antibodies are described in U.S. Pat. Nos. Re. 31,006, 3,654,090, 4,214,048, 4,289,747, 4,302,438, 4,312,943, 4,376,110 and the references cited therein, for example. Examples of other suitable systems are described by Pesce et al, *Clin.Chem.* 20(3):353–359 (1974) and Wisdom, G., *Clin.Chem.* 22:1243 (1976).

A list of suitable enzyme classes and specific examples for each class follow

TABLE B

| Class | Enzyme Example |
|---|---|
| Hydrolases Carbohydroases | Amylases |
| Nucleases | Polynucleotidase |
| Amidases | Arginase |
| Purine deaminases | Adenase |
| Peptidases | Aminopolypeptidase |
| Proteinases | Pepsin |
| Esterases | Lipases |
| Iron Enzymes | Catalase |
| Copper Enzymes | Tyrosinases |
| Enzymes containing Coenzymes | Alcohol dehydrogenase |
| Enzymes reducing cytochrome | Succinic dehydrogenase |
| Yellow enzymes | Diaphorase |
| Mutases | Glyoxalase |
| Demolases | Aldolase |
| Oxidases | Glucose oxidase |
|  | Horse radish peroxidase |
| Other enzymes | Beta-galactosidase |
|  | Phosphatases |
|  | Phosphorylases |
|  | Hexokinases |

A list of suitable enzymes are described in Hawk, et al. PRACTICAL PHYSIOLOGICAL CHEMISTRY, New York: McGraw-Hill pp. 306–397 (1954).

Fluorogenic enzymes (enzymes in the presence of which a selected substrate will produce a fluorescent product) are also highly useful labeling moieties. Methods for selectively conjugating enzymes to antibodies without impairing the ability of the antibody to bind with antigen are well known in the art. Suitable enzymes and procedures for coupling them to antibodies are described by Wilson, M. et al, "Recent developments in the periodate method for conjugating horseradish peroxidase (HRPO) to antibodies." INTERNATIONAL CONFERENCE IN IMMUNOFLUORESCENCE AND RELATED STAINING TECHNIQUES. W. Knapp et al, editors. Amsterdam: Elsevier pp 215–244 (1978), Sullivan, M. et "Enzyme immunoassay: a review." *Annals of Clinical Biochemistry*. 16:221–240 (1979), and in U.S. Pat. No. 4,190,496, for example. The preferred fluorogenic enzymes and suitable substrates corresponding thereto include horseradish peroxidase for which a suitable substrate is homovanillic acid or 4-hydroxy-3-methoxy-phenylacetic acid, beta-galactosidase for which a suitable substrate is 4-methylumbelliferylbeta-D-galactoside, alkaline phosphatase for which a suitable substrate is 4-methylumbelliferyl phosphate and other umbelliferyl phosphates such as 4-carboxyumbelliferyl phosphate and umbelliferyl phosphate 4-carboxyalkyl esters, etc.

Examples of suitable procedures for enzyme labeling the antibody include the use of carbodiimides, dialdehydes, and bifunctional coupling reagents. Linkage of enzymes through amide groups can be achieved by treating the proteins with thionyl chloride, N-hydroxysuccinimide or similar reagents in an anhydrous solvent such as dimethylformamide, dioxane, dimethylsulfoxide, tetrahydrofuran and the like. Alternative coupling agents include carbodiimides such as 1-ethyl-3-(3-N,N'-dimethylaminopropyl)carbodiimide or 1-cyclohexyl-3-(2-morpholinoethyl)carbodiimide methyl-p-toluenesulfonate.

The carbohydrate moiety of an enzyme can also be oxidized to an aldehyde and reacted with lysyl amino groups of immunoglobulins to form a Schiffs base. Reduction with sodium borohydride effects a stable linkage of enzyme and antibody. Horseradish peroxidase with antibody can be efficiently linked to immunoglobulins by the method of Wilson, supra.

Fluorescent labeled antibodies can be prepared from standard fluorescent moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers are described by Stryer, *Science*. 162:526 (1968) and Brand, L. et al, "Fluorescent probes for structure," *Annual Review of Biochemistry*. 41:843–868 (1972). The anti-CK-MM antibodies of this invention can be labeled with fluorescent groups by conventional procedures such as those disclosed in U.S. Pat. Nos. 3,940,475, 4,289,747 and 4,376,110, for example.

One group of fluorescers having a number of the desirable properties described above are the xanthene dyes, which include the fluoresceins derived from 3,6-dihydroxy-9-phenylxanthhydrol and resamines and rhodamine group derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available.

Another group of fluorescent compounds are the naphthylamines, having an amino group in the alpha or beta position. Included among the naphthylamino compounds are 1-dimethylaminonaphthyl-5-sulfonate, 1-anilino-8-naphthalene sulfonate and 2-p-toluidinyl-6-naphthalene sulfonate. Other dyes include 3-phenyl-7-isocyanatocoumarin; acridines such as 9-isothiocyanatoacridine and acridine orange; N-[p-(2-benzoxazolyl)phenyl]maleimide; benzoxadiozoles such as 4-chloro-7-nitrobenzo-2-oxa-1,3-diazole and 7-(p-methoxybenzylamino)-4-nitrobenzo-2-oxa-1,3-diazole; stilbenes such as 4-dimethylamino-4'-isothiocyanatostilbene and 4-dimethylanimo-4'-maleimidostilbene; N,N'-dioctadecycloxacarboxyamine-p-toluenesulfonate; pyrenes such as 8-hydroxy-1,3,6-pyrenetrisulfonic acid, 1-pyrenebutyric acid, merocyanine 540, rose bengal, 2,4-diphenyl-3(2H)-furanone, o-phthaldehyde, as well as other readily available fluorescing molecules. These dyes either have active functionalities or such functionalities can be readily introduced.

For example, antibodies can be labeled with fluorochromes by the procedures described by Goding, J. MONOCLONAL ANTIBODIES: PRINCIPLES AND PRACTICE. New York: Academic Press, pp 208–249 (1983). The concentration of fluorochrome is selected according to the table of Goding, p 229. For example, fluorescein isocyanate (1.0 mg/ml) or rhodamine isocyanate (10.0 mg/ml) in DMSO is prepared, and the desired volume (1–10% of total protein solution volume) is added to the protein solution dropwise, with stirring. The reaction proceeds for two hours, shielded from light. The product is purified by gel filtration on SEPHADEX G-25 gel in PBS containing 0.1% $NaN_3$ to separate the unreacted or hydrolyzed fluorochrome. The absorbence of the conjugate i measured at 280 nm and at its peak in the visible region (495 nm for fluoresceinated antibody and 550 nm for rhodaminated antibody). The fluorochrome to protein ratio is calculated according to the procedure of Goding, supra, p 224–225. Conjugates are stored at 4° C. protected from light until use. If the antibody solution concentration is less than 1 mg/ml, BSA is added to the solution to a final concentration of 1 mg/ml.

The anti-CK-MM antibodies can be covalently bonded to avidin or biotin in one embodiment of this invention. Suitable binding procedures involve cross-linking through a bifunctional cross-linking agent. Suitable bifunctional compounds are described by Peters, K. et al *Ann.Rev.Biochim.* 46:523 (1977). Alkyl imidates show a high degree of specificity among the functional groups presented to them by a protein. The reaction is specific for primary amino groups. Examples of suitable coupling reagents include amidoesters such as dimethylmalonimidate, azides such as the acyl azide of tartryl diazide which reacts readily with immuno groups to produce amide linkages. Aryl dihalides (e.g., 1,5-difluoro-2,4-dinitrobenzene, or 4,4'-difluoro-3,3'-dinitrophenyl sulfone, glutaraldehyde, 1-ethyl-3-(3-dimethylaminopropyl)carbodiimide hydrochloride, dimaleimide, mixed anhydride, m-maleamidobenzoyl N-hydroxysucciinimide ester, and other known cross-linking agents.

The foregoing reagents provide essentially irreversible bonds. Bifunctional agents with functional groups such as disulfide or glycol may be used. These provide bonds which can be broken after the cross-linking reaction, if desired. Such reagents include dimethyl 3,3'-dithiobispropionimidate, succinimidyl propionimidate, N-(3-fluoro-4,6-dinitrophenyl)-cystamine, tartryl diazide, tartryl di(glycylazide) and tartryl di(epsilon-amino caproylazide).

In other instances, the bonds can be formed directly between the reagents themselves. For example, antibody can be bound to biotin through functional groups on the respective materials. As a specific example, biotin can be treated with periodate and reacted with antibody to give a Schiff base formation without inhibiting the biotin to avidin binding or blocking immunological activity of the antibody.

Known techniques using bifunctional cross-linking agents include the following: (a) a one-step glutaraldehyde linkage, Avrameas, S., *Immunochemistry*. 6:43 (1969); (b) two-step glutaraldehyde linkage, Avrameas, S., *Immunochemistry*. 8:1175 (1971); and (c) dimaleimide linkage, Kato, K. et al, *Euro.J.Biochem.* 62:285 (1966).

Antibodies can be labeled with metallic radionuclides according the procedure of Hnatowich, D. et al. *Journal of Applied Radiation.* 35(6):554–557 (1984) and Buckley, R et al. *Federation of European Biochemical Societies.* 166(1):202–204 (Jan. 1984). In this procedure the antibodies are conjugated with a chelating agent such as diethylenetriamine pentaacetic acid which is capable of forming a chelate with the metallic radionuclide. A suspension of 0.1 mg/ml of the bicyclic anhydride of DTPA (diethylenetriamine pentaacetic acid) is prepared in a dry solvent such as chloroform, ether or dry DMSO. An aliquot is removed to a clean, dry tube sufficient to provide a DTPA to immunoglobulin molar ratio of 1:1 and evaporated under nitrogen. A 10–20 microliter portion of the antibody solution used (10–20 mg/ml) in 0.05M bicarbonate buffer in saline, pH 7.0–7.5 is added to the dry DTPA, and the contents are agitated for 0.5–1.0 min. The coupled protein preparation is diluted to 0.2 ml with the same buffer solution and purified on a 5 cm gel filtration column with SEPHADEX G-50 gel, using a saline eluant. The coupling efficiency is determined before purification by the addition of "chelation-grade" $^{111}In$ in 0.5M acetate buffer solution, pH 6.0. Thin layer chromatography is used to separate the DTPA coupled antibody for calculation of the coupling efficiency. The DTPA-coupled antibodies can be stored at 4C until needed for binding with metallic radionuclides.

Examples of other suitable labels are described by Voller, A. et al. IMMUNOASSAYS FOR THE 80s. Baltimore: University Park Press (1981),and U.S. Pat. Nos. 4,220,450 and 3,960,834, the entire contents of which and the references cited therein being hereby incorporated by reference. One such example is a chemiluminescence label described by McCapra, *Quarterly Reviews.* 20:485 (1966), U.S. Pat. No. 4,220,450, and Voller (supra, pp 113–125).

CK REAGENTS

In competition assay embodiments of this invention, a labeled $CK-MM_A$ or $CK-MM_{(A+B)}$ is used. In general, these isoforms can be conjugated with the labels described above for preparing a labeled antibody, and the covalent bonding methods for attaching the label moiety to the antibody can be the same for preparing the labeled protein. Enzyme labeled and radiolabeled CK reagents are particularly useful.

ASSAY METHODS

One aspect of the method of this invention includes a step of contacting an anti-($CK-MM_A$) antibody with patient serum to effect conjugation of CK-MM$_A$ in the sample with the antibody. Another aspect of the method of this invention includes a step of contacting an anti-(CK-MM$_{(A+B)}$) antibody or a mixture of anti-(CK-MM$_A$) antibodies and of anti-(CK-MM$_B$) antibodies with patient serum to effect conjugation of CK-MM$_A$ and CK-MM$_B$ in the sample with the antibodies.

In the sandwich immunoassays of this invention, the CK-MM isoform being assayed is insolubilized by conjugating it with a suitably binding antibody bound to an insoluble support.

In one embodiment, an anti-MM antibody is bound to the insoluble support, the CK-MM isoforms are insolubilized by contacting the insolubilized antibodies with the serum sample. The antibodies on the insoluble support is then selectively conjugated with labeled anti-(MM$_A$) antibody, or with labeled anti-(CK-MM$_{(A+B)}$) antibody or a mixture of labeled anti-(CK-MM$_A$) antibodies and of labeled anti-(CK-MM$_B$) antibodies, for the determination of the CK-MM$_A$ or the combined CK-MM$_A$ and CK-MM$_B$ levels in the sample, respectively. This embodiment comprises (a) contacting the serum sample or an aqueous dilution thereof with an insoluble support to which anti-(CK-MM) antibody is bound for a time sufficient to permit binding between the antibody and CK-MM compounds in the solution and removing the aqueous solution;

(b) contacting the insoluble support with a solution of a labeled anti-(CK-MM subtype) antibody for a time sufficient to permit antibody bonding with CK-MM subtype or subtypes bound to the insoluble support and removing the solution from the support, and (c) determining the labeled antibody bound to the insoluble support.

In the other embodiment of the sandwich assay of this invention, the selectively binding antibody, i.e., anti-(CK-MM$_A$) antibody, anti-(CK-MM$_{(A+B)}$) antibody or a mixture of anti-(CK-MM$_A$) antibodies and of anti-(CK-MM$_B$) antibodies, are bound to the insoluble support. The corresponding CK-MM isoforms are insolubilized by contacting the sample with the insoluble support. The antibodies conjugated to the insoluble support can then be determined by conjugating them with a labeled anti-MM antibody or by testing the activity (enzyme activity) of the material bound to the insoluble support. The labeled antibody embodiment comprises (a) contacting the serum sample or an aqueous dilution thereof with an insoluble support to which anti-(CK-MM subtype) antibody is bound for a time sufficient to permit binding between the antibody and CK-MM subtype or subtypes in the solution and removing the aqueous solution;

(b) contacting the insoluble support with a solution of a labeled anti-(CK-MM) antibody for a time sufficient to permit antibody bonding with CK-MM subtype or subtypes bound to the insoluble support and removing the solution from the support, and (c) determining the labeled antibody bound to the insoluble support.

In the enzyme activity measurement embodiment, the insoluble support is contacted with a substrate or other material which, in the presence of the enzyme, yields a physically detectable product such as a chromophore.

In a competition immunoassay of this invention, the selectively binding antibody, i.e., anti-(CK-MM$_A$) antibody, anti-(CK-MM$_{(A+B)}$) antibody or a mixture of anti-(CK-MM$_A$) antibodies and of anti-(CK-MM$_B$) antibodies, are bound to the insoluble support. In one embodiment, the insoluble support is then contacted with a mixture of the serum sample and labeled CK-MM isoform for which the sample is being assayed, and the labeled material remaining in the solution or bound to the insoluble support is measured. This embodiment comprises (a) contacting a mixture of serum sample and a predetermined amount of labeled CK-MM isoform with an insoluble support to which the anti-(CK-MM isoform) antibody is bound for a time sufficient to permit binding between the antibody and CK-MM isoform and separating the insoluble support from the liquid phase, and (b) determining the amount of labeled CK-MM isoform present on the insoluble support or remaining in the liquid phase.

In another embodiment, the insoluble support to which the CK-MM isoform being assayed is adhered is contacted with a mixture of the serum sample and labeled anti-(CK-MM isoform) antibody corresponding to the CK-isoform being assayed, and the labeled material remaining in the solution or bound to the insoluble support is measured. This embodiment comprises (a) contacting a mixture of serum sample and a predetermined amount of labeled anti-(CK-MM isoform) antibody with an insoluble support to which reagent CK-MM isoform is bound for a time sufficient to permit binding between the antibody and CK-MM isoform and separating the insoluble support from the liquid phase, and (b) determining the amount of labeled anti-(CK-MM isoform) antibody present on the insoluble support or remaining in the liquid phase.

In the above methods, the insoluble supports with the antibodies bound thereto are important aspects of this invention.

Suitable incubation times for conjugation o anti-(CK-MM) antibodies with CK-MM isoforms are from 30 to 240 minutes at temperatures within the range of from 16° to 40° C., the preferred contact time being at least 60 minutes at temperatures within the range of from 20° to 26° C.

A wide variety of compounds can be employed as the solid support, the primary consideration being the binding of the antibody or protein to the surface, the absence of interference with the reactions of the label with reagents used to develop it, and the absence of interference with the examination of the developed label. In particular, if fluorescence or chromogenic spectrum is being measured, the insoluble support should not provide interference.

Organic and inorganic polymers, both natural and synthetic can be employed as the solid support. Examples of suitable polymers include polyethylene, polypropylene, polybutylene, poly(4-methylbutylene), butyl rubber and other synthetic rubbers, silicone rubbers and silastic polymers, polyesters, polyamides, cellulose and cellulose derivatives (such as cellulose acetate, nitrocellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, styrene-acrylonitrile copolymers, rayon, nylon, polyvinylbutyrate, polyformaldehyde, etc. Other materials which can be employed as the insoluble support are silica gel, silicon wafers, glass, paper, insoluble protein, metals, metalloids, metal oxides, magnetic materials, semi-conductive materials, cermets or the like. In addition are included substances that form gels, such as proteins such as gelatins, lipopolysaccharides, silicates, agarose, polyacrylamides or polymers which form several aqueous phases such as dextrans, polyalkylene glycols (alkylene with 2 to 3 carbon atoms) or surfactants, e.g. amphophilic compounds such as phospholipids, long chain (12-24 carbon atoms) alkyl ammonium salts and the like.

A preferred diagnostic support of this invention comprises polystyrene, styrene copolymers including styrene-(vinyl monomer) copolymers such as styrene-acrylonitrile copolymers, polyolefins such as polyethylene and polypropylene, and acrylate and methacrylate polymers and copolymers.

The antibody can be bound to the support by any method of bonding which does not significantly reduce the antibody binding sites and which binds sufficiently to permit separation of the insoluble support from the liquids and rinse solutions without significant detachment of antibody from the surface of the support. Non-covalent bonding can be achieved by adsorption, ionic bonding, van der Waals adsorption, electrostatic bonding, other non-covalent bonding. The antibody can also be bound to the support by covalent bonding. A particularly advantageous support for this procedure comprises a microtiter plate having a plurality of wells. The well surface, or nitrocellulose or plastic cup inserts of other material therein can constitute the antibody support.

In a procedure for non-covalent adhesion of antibody to the surface of an insoluble support, the antibody material can be applied to the surface of a support such as a polystyrene microtiter well or polystyrene individual insert well therefor, in an aqueous buffer solution. The surface is initially cleaned with a cleaning fluid such as methanol and dried. The buffered antibody solution is placed in the well or insert cup and incubated at room temperature until adsorption occurs, for example for from 2 to 18 hours and preferable from 16-18 hours, at temperatures of from 4 to 40C. and preferable from 20 to 26C. The well is then rinsed with a weak saline solution and dried. Other procedures for covalently adhering antibodies to insoluble supports are described by Ichiro Chibata in *Immobilized Enzymes*, Halsted Press, New York, 1978, and by A. Cuatrecasas, *J.Bio.Chem.* 245 3059(1970), the entire contents of which are hereby incorporated by reference. The surface can be coated with a protein and coupled with antibody using the procedures described in U.S. Pat. 4,210,418 using glutaraldehyde as a coupling agent, for example. In a still further procedure, the well can be coated with a layer having free isocyanate groups such as a polyether isocyanate, and application of the antibody in aqueous solution thereto effects the requisite bonding. In a still further procedure, the antibody can be coupled to a hydroxylated material by means of cyanogen bromide as described in U.S. Pat. No. 3,720,760. In a still further procedure, Staphococcus Protein A can be bound to the insoluble support, and the $F_c$ chain of the antibody can be conjugated with the Protein A.

Removal of solutions from solid surfaces is facilitated by applying a rinse solution. The rinse solutions, samples and all process solutions in which CK-MM enzymes are present should preferably contain a chelating agent such as EDTA to stabilize the enzyme and any conversion factor which could convert it to another form. A suitable rinse solution is an aqueous phosphate buffer solution having a phosphate molarity of from 0.01 to 0.05, a pH of from 6 to 8 and containing from 0.01 to 0.01 weight percent non-ionic surfactant. Suitable non-ionic surfactants include polyoxyethylene ethers (BRIJ) such as lauryl, cetyl, oleyl, stearyl, and tridecyl polyoxyethylene ethers; polyoxyethylenesorbitans (TWEEN) such as polyoxyethylenesorbitan monolaurate, monopalmitate, monostearate, monoleate and trioleates; and other polyoxyethylene ethers (TRITON), for example. A preferred non-ionic surfactant is octylphenoxypolyethoxy ethanol having 40 ethylene oxide units (TRITON X-405, Rohm and Haas Company).

In embodiments using a second antibody-antigen conjugation, the insoluble surface is contacted with the support in the same manner as described above with regard to the first antibody-antigen conjugation, with the exception that the conjugation is conducted with a substantial excess of the second antibody, and the conjugation reaction is allowed to proceed until substantially all of the first antibody on the insoluble support is reacted with second antibody.

The final step in all embodiments of this invention is the determination of the presence of an antibody or labeled CK-MM isoform, either on or in an insoluble material or in a solution. The manner of determining the antibody or CK-MM isoform is different for each type of labeled reagent used. Procedures for label determinations are well established in the art, for example as described by Voller et al, supra.

If the target moiety to be measured is an unlabeled antibody bound to the insoluble support, the preferred manner of determination of the target moiety involves contacting the insoluble support with a solution of labeled Protein A or a labeled secondary antibody which will conjugate with the primary antibody. Suitable antibodies include labeled secondary antibodies which bind with the Fc portion of primary antibodies.

Both monoclonal and polyclonal secondary antibodies which bind to the Fc portion of other antibodies and labeled Protein A are readily available from commercial sources. These can be distinctively labeled in the same manner as described above for labeling the primary antibodies. Suitable examples are described by D. Catty, et al in "Antisera in Immunoassays with special Reference to Monoclonal Antibodies to Human Immunoglobulins", *Immunoassay's for the 80,s,* supra, pp 133-153 and the publications cited therein, the entire contents of which are hereby incorporated by reference.

In the preferred embodiments of this invention, the presence and amount of a labeled antibody or labeled CK-MM isoform is determined. Labels which can be directly observed or measured are the most easily determined, and a wide variety of manual, semi-automatic and automatic analyzers are available for increasing the efficiency of the analysis. Examples of such labels are radiolabels which can be measured with radiation counting devices; pigments, dyes or other chromogens which can be visually observed or measured with a spectrophotometer; spin labels which can be measured with a spin label analyzer; and fluorescent moieties which can be visualized under ultraviolet light or can be measured with standard fluorometers, for example. The label can be a luminescent substance such as a phosphor or fluorogen, a bioluminescent substance, a chemiluminescent substance or a metal containing substance.

Amplification and greater distinctions from background can be achieved by use of enzyme labels or enzyme labeling systems. The substrate is selected to yield the preferred measurable product. Chromogenic and fluorogenic enzymes are preferred. These are enzymes for which substrates yielding chromogen and fluorogens, respectively, are known.

A preferred chromogenic substrate and an enzyme uses oxidoreductases such as horseradish peroxidase and a substrate such as diaminobenzidine which yields a distinguishing color. Any other enzyme-chromogen yielding substrate combination can be used if it provides distinguishing pigmentation.

Enzyme combinations with fluorogen substrates which can be used are described in U.S. Pat. No. 4,190,496, for example, the contents thereof being hereby incorporated by reference. The preferred fluorogenic enzymes and the suitable substrates corresponding thereto include horse-radish peroxidase for which a suitable substrate is homovanillic acid or 4-hydroxy-3-methoxyphenylacetic acid, beta-galactosidase for which a suitable substrate is 4-methylumbelliferyl-beta-D-galactoside, alkaline phosphatase for which a suitable substrate is 4-methylumbelliferyl phosphate and other umbelliferyl phosphates such as 4-carboxyumbellifery phosphate, and umbelliferyl phosphate 4-carboxy alkylesters, etc.

To develop the chromogen or fluorogen, the solid is contacted with an aqueous solution of the substrate containing from $10^{-2}$ to $10^{-10}$ molar and preferably from $10^{-4}$ to $10^{-5}$ molar concentrations of the substrate. Preferred additional reagents and buffers in the substrate solution include 2-amino-2-methyl-1-propanol buffer and magnesium chloride, for example.

The substrate solution is incubated with the insoluble support for sufficient time for the fluorescent reaction product to form. At temperatures of from 18 to 40C., incubation times of from 5 to 240 minutes can be used. Preferably, the temperature is within the range of from 20 to 26C., and the incubation time is from 30 to 90 minutes.

For further amplification, an immunoperoxidase method using biotin-avidin complexes can be used. This procedure uses a biotin labeled antibody. The biotin is covalently bonded to the secondary antibody by conventional procedures such as those described above for binding enzymes to the primary antibody with a large molar excess of biotin to antibody, preferably with a molar ratio of at least 100:1 biotin to enzyme.

A preferred biotin-avidin complex includes avidin and a biotinylated enzyme. The enzyme can be one of the enzymes previously described. Avidin-biotin systems using immunoperoxidase techniques are described by Hsu, S. et al in *The Journal of Histochemistry and Cytochemistry.* 29(4):577–580 (1981), *Am.J.Clin.Path.* 75(5):734–738 (1981), and *Am.J.Clin.Path.* 75(6):816–821 (1981). Systems applying avidin-biotin systems also commercially available from Vector Laboratories, Inc. of Burlingame, Calif. and are described in their customer literature.

The rinsed support to which biotin labeled antibody may be bound is contacted with an avidin-(labeled biotin) complex. The preferred avidin-biotin complex is prepared by mixing a large molar excess of avidin with the biotinylated enzyme. The biotin can also be labeled with other conventional labels such as a luminescent substance such as a phosphor or fluorogen, a bioluminescent substance, a chemiluminescent substance, a radioactive substance, an enzyme, chromophor, pigment, spin label, or metal containing substance. These labels are covalently bonded to the biotin by conventional procedures appropriate to the chemical groups on the label and which have been described above for applying the same labels to antibody reagents.

The avidin-biotin complex is applied to the insoluble support in a suitable aqueous buffer solution such as the PBS solutions described above for applying antibodies to the insoluble support. The complex solution is applied for a time sufficient to permit binding of the avidin-biotin complex with the biotin which is present on the support, if any. Following this step, the excess avidin-biotin complex solution is removed, and the insoluble support is preferably rinsed with a suitable rinse solution such as the rinse solution described above, for example.

The insoluble support is then examined by procedures appropriate for the particular avidin-biotin complex label employed. These procedures are conventional. For example, if a radioactive label is employed, the insoluble support can be examined with a Geiger counter to measure the level of residual radioactivity on the insoluble support. Alternatively, if the label is a phosphor or a fluorogen, it can be examined under a fluorescent microscope. If the label is a chromophor or a pigment, the insoluble support can be examined under a microscope using ordinary light.

In embodiments wherein the last step is the measurement of enzymatic activity of CK-MM isofilms bound to the insoluble support, the insoluble support can be contacted with an aqueous solution of a substrate which, in the presence of the CK-MM enzyme, will yield a physically detectable product. Suitable substrates are described in U.S. Pat. Nos. 3,994,783, 4,012,285, 4,067,775 and 4,260,678, the entire contents of these patents and the patents and other publications listed therein being hereby incorporated by reference in their entireties. In one procedure, CK specifically catalyzes the transphosphorylation of ADP to ATP. Hexokinase is used to catalyze the phosphorylation of ATP and glucose to glucose-6-phosphate. Glucose-6-phosphate is then oxidized and NAD reduced in the presence of glucose-6-phosphate dehydrogenase (G6PD) to 6-phosphogluconate and NADH. Nitro blue tetrazoleum (NBT) is added at the end of a timed incubation. NADH reduces NBT to a colored formazan with maximum absorbance at 530 nm. 1-Methoxy phenazine methosulfate (MPMS) catalyzes formazan production. This procedure is described by Nachlas, M., et al, *Anal.-Biochem.* 1:317 (1960), and the DATA-ZYME reagents therefor are available from Data Medicxal Associates, Inc., 2016 East Randol Mill Road, Arlington, Tex.

This invention is further illustrated by the following specific, but non-limiting examples. Temperatures are provided in degrees Centigrade and concentrations as weight percents unless otherwise indicated. Examples which are constructively reduced to practice herein are presented in the presence tense, and examples which represent work which has been reduced to practice in the laboratory is presented in the past tense.

EXAMPLE 1

Preparation of Polyclonal Anti-(CK-MM) Antibodies

Purified CK-MM isoenzyme (Diagnostic Biochemicals Laboratories, Dallas, Tex.), 250 μg (micrograms), in Freund's adjuvant was used to immunize rabbits, injecting at two week intervals. Test bleeds were checked for antibody activity after ten weeks of immunization. Antiserum was collected over several months until an acceptable antibody titer was obtained. The antibody reacted to all isoforms of CK-MM, i.e., CK-$MM_A$, CK-$MM_B$, CK-$MM_C$.

EXAMPLE 2

Preparation of Polyclonal Anti-(CK-$MM_A$) Antibodies

CK-$MM_A$ isoform is obtained from total CK-MM heart extract by the method of Vaidya, et al, *Biochimica et Biophysica Acta.* 790:230-237 (1984). The procedure of Example 1 is repeated with the CK-$MM_A$ isoform to yield antiserum containing a mixture of antibodies.

In the following chromatographic separation, all solutions should preferably containing a chelating agent such as EDTA to stabilize the CK-MM isoform. A column prepared by the procedures described in AFFINITY CHROMATOGRAPH: PRINCIPLES AND METHODS. Pharmacia Fine Chemicals, AB, Box 175 S-75104 Uppsula, Sweden (1971), the entire contents of which are hereby incorporated by reference in its entirety. The column is packed with 25 ml of SEPHAROSE gel conjugated to CK-$MM_A$ isoform as follows: Freeze-dried CNBr-SEPHAROSE 4B powder (Pharmacia) is swelled for 15 min in 1 mM HCl. The gel is washed on a sintered glass filter (porosity G-3) with a total of 200 ml of 1 mM HCl per gram of gel (dry wt.) This is done in several aliquots, the supernatant being suctioned off between successive additions. 5 mg of CK-$MM_A$ per 1 ml of gel is dissolved in Coupling Buffer (0.1M $NaHCO_3$, pH 8.3, containing 0.5M NaCl) containing EDTA. The gel is washed with Coupling Buffer, the excess is removed by suction, and the enzyme solution is mixed with the gel. The mixture is allowed to stand overnight at 4° C. without stirring. The gel is then placed in a Blocking Buffer containing 1M ethanolamine, pH 8.0, for 2 hr at rm temp. The gel is then washed with the Coupling Buffer, 0.1M Acetate Buffer, pH 4.0, containing 0.5M NaCl, and washed twice with Coupling Buffer. The enzyme protein-SEPHAROSE conjugate is now ready for use and can be stored at 4° to 8° C. Cyanogen bromide can be added to the buffer solution as a bacteriostat.

The column is equilibrated with from 2 to 3 volumes of buffer (0.15M PBS, pH 7.2), and the sample is then applied to the column. The eluted fractions containing antibody are collected until peak activity disappears.

The column is then washed with 10× volumes of 0.15 PBS buffer, pH 7.2.

The column is then washed with distilled water to desorb immunoaffinity bound antibody. HPLC grade distilled water is perfused through the column in a volume equal to the void volume, and elution is stopped for 6 hr. The column is then eluted with additional distilled water at a rate of 15-20 ml/hr, collecting the eluted samples and retaining peak fractions. The peak fractions are dialyzed against 0.15M PBS, pH 7.2, for 24-36 hr at 4° C. with multiple buffer changes.

This procedure is repeated with the eluant with affinity columns to which CK-$MM_B$, CK-$MM_C$ and CK-MB is bound, to yield an ultimate eluant containing anti-(CK-$MM_A$) antibodies which do not significantly bind with CK-$MM_B$, CK-$MM_C$ and CK-MB isoforms.

EXAMPLE 3

Preparation of Polyclonal Anti-(CK-$MM_B$) Antibodies

CK-$MM_B$ isoform is obtained from total CK-MM heart extract by the method of Vaidya, et al, *Biochimica et Biophysica Acta.* 790:230-237 (1984). The immunization procedure of Example 2 is repeated with the CK-$MM_A$ isoform to yield antiserum containing a mixture of antibodies.

A column is packed with 25 ml of SEPHAROSE gel conjugated to CK-$MM_B$ isotype as described in Example 2. The column is equilibrated with from 2 to 3 volumes of buffer (0.15M PBS, pH 7.2), and the sample is then applied to the column. The eluted fractions containing antibody are collected until peak activity disappears.

The column is then washed with 10× volumes of 0.15 PBS buffer, pH 7.2. The column is then washed with distilled water to desorb immunoaffinity bound antibody. HPLC grade distilled water is perfused through the column in a volume equal to the void volume, and elution is stopped for 6 hr. The column is then eluted with additional distilled water at a rate of 15-20 ml/hr, collecting the eluted samples and retaining peak fractions. The peak fractions are dialyzed against 0.15M PBS, pH 7.2, for 24-36 hr at 4° C. with multiple buffer changes.

This procedure is repeated with the eluant with affinity columns to which CK-$MM_A$, CK-$MM_C$ and CK-MB is bound, to yield an ultimate eluant containing anti-(CK-$MM_B$) antibodies which do not significantly bind with CK-$MM_A$, CK-$MM_C$ and CK-MB isoforms.

EXAMPLE 4

Preparation of Monoclonal and Antibodies 9 and 19

1. Immunization protocol

Eight week old female A/J mice, H-2a haplotype (Jackson Laboratories, Bar Harbor, ME) were primed intraperitoneally with 25 μg of purified CK-$MM_A$ emulsified in complete Freund's adjuvant. 5 Weeks and 8.5 weeks later, mice were boosted intravenously with 10 μg of purified CK-$MM_A$. 3 Days after the final booster immunization, the mouse was sacrificed and the spleen removed for fusion.

2. Cell fusion

Spleen cells obtained from the immunized mouse were fused with a Balb/C myeloma cell line essentially as described by Kohler and Milstein, *Nature.* 256:495-497 (1975) using polyethylene glycol (NEN Products, Boston, Mass.) as fusion agent. The fused cells were cultured in 96-well culture plates and incubated at 37° C. in an atmosphere containing 5 vol. % $CO_2$.

3. Screening for antibodies

Culture supernatants from individual wells were screened for antibodies that react with CK-MM using solid-phase radioimmunoassay on post fusion day 8. A 100 μl (microliter) volume of culture supernatant was incubated with an equal volume of either $^{125}$I-CK-$MM_A$ or $^{125}$I-CK-$MM_C$ (50,000 cpm) in 96 well plates (IMMULON II, Dynatech Laboratories, Alexandria, Va.) previously coated with goat anti-mouse IgG antibodies (Pal-Freeze Biologicals, Rogers, Ark.). After 2-3 hr incubation at room temperature, the plates were rinsed 3 times with TWEEN-PBS, blotted dry and the radioactivity of the bound $^{125}$I-CK-MM$_A$ was counted with a gamma counter.

4. Culture expansion and hybridoma cloning

Hybridoma culture producing antibodies that react with CK-MM$_A$ and CK-MM$_C$ were expanded into 24-well culture plates and 25 cm$^2$ tissue culture flasks. Cloning by limiting dilution was subsequently performed, and the cloned hybridomas secreting antibodies that react with CK-MM were further expanded.

5. Production of ascites

8 Wk old female CAF$_1$/J mice (Jackson Laboratories, Bar Harbor, Me.) primed with incomplete Freund's adjuvant were injected intraperitoneally with $10^5$–$10^6$ hybridoma cells. Ascites were harvested 10–14 days later.

6. Purification of monoclonal antibodies

Ascites were centrifuged to remove cells and debris. An equal volume of 1,1,2-trichloro-1,2,2-trifluoroethane (Mallinckrodt, Paris, Ky.) was combined with the cell-free ascites and vigorously agitated for 10–20 min. The mixture was centrifuged to separate antibody-containing ascites from the lipid layer. The lipid-extracted ascites were heat treated (56° C., 30 min), added with 0.1% NaN$_3$, and kept at −20° C. or further purified. For further purification, ascites were precipitated with 50% saturation of ammonium sulfate, centrifuged, and the precipitates were dialyzed against 20 mM phosphate buffer, containing 15 mM NaCl, pH 7.2. For DGAE chromatography, one-step elution was carried out to obtain the IgG monoclonal antibody enriched fraction. A column was packed with DE52 (Whatman, England), was equilibrated with 20 mM phosphate buffer, 15 mM NaCl, pH 7.2, and was loaded with the dialyzed monoclonal antibody preparation at a ratio of 4 ng of protein to 1 ml of DE52 matrix. It was eluted with the same buffer, greater than 90% of the total antibody activity being eluted unbound. Nevertheless, different monoclonal antibodies appeared to behave somewhat differently with regard to the elution patterns. Therefore, a stepwise increment of salt concentration for elution is recommended.

EXAMPLE 5

Radioactive Labeling of Monoclonal Antibodies

Polyclonal and monoclonal antibodies are labeled with $^{125}$I using the "ionogen" method of Fraker, P. et al, *Biochem.Biophys.Res.Commun.* 80:849 (1978), modified as described in U.S. Pat. No. 4,624,916, the contents of which are hereby incorporated by reference in its entirety.

EXAMPLE 6

Evaluating Reactivity of Monoclonal Antibodies

Rabbit anti-(CK-MM) antibody prepared in accordance with Example 1 is immobilized on magnetic latex particles (polystyrene particles, Seragen, Indianapolis, Ind.). Goat anti-rabbit (IgG) antibodies were passively absorbed on latex by known methods. Rabbit anti-CK-MM was then reacted to provide solid-phase rabbit anti-CK-MM. The suspension of this solid-phase (100 μl) is mixed with a sample of CK-MM$_A$ exposed to human serum containing conversion factors for various lengths of time at 37° C. The $^{125}$I labeled monoclonal antibody prepared in accordance with the procedure of Example 5 is also added (100–130,000 counts per min). The immunological assay procedure was as follows:

1. Allow assay reagents to come to room temperature.
2. Label test tubes in duplicate for each calibrator, control and patient sample.
3. Pipette 25 μl of each calibrator, control and sample directly into the bottom of each tube.
4. Pipette 100 μl of $^{125}$I-labeled antibody reagent made in according to the procedure of Example 5 into the bottom of each tube.
5. Mix the solid-phase reagent consisting of immobilized rabbit anti-(CK-MM) antibody gently and pipette 25 μl of the suspension into each tube.
6. Shake the test tube rack to mix the contents well.
7. Incubate tubes at room temperature for 15 minutes on a rotator at 150–170 rpm.
8. Dispense 1 ml of wash buffer into all tubes.
9. Place test tubes into a magnetic rack.
10. Aspirate or decant liquid from all tubes.
11. Count all tubes in a gamma counter for one minute with the window suitably adjusted for iodine-125.
12. Calculate results. Calculate the average counts per minute (CPM) for all calibrators. Plot a calibration curve on the graph paper provided with the CPM on the y-axis and CK-MM$_A$ and CK-MM$_B$ concentration on the x-axis. Draw a best fitting curve. Read the concentration of each sample from the calibration curve.

The tests were compared with results obtained with electrophoretic separation of CK-MM isoforms, separated as follows. To each thawed plasma sample, 50 μl of buffer containing 200 mM EDTA, 100 mM MET in 10 mM TrisHCl buffer, pH 7.4, was added. One microliter of the sample is then applied to each well of a Corning Electro-Trace Special purpose electrophoresis film, 1% agarose (Corning, Palo Alto, Calif. Catalog 470104). Electrophoresis buffer consisted of 97% (v/v) 50 mM Tris Barbitol Buffer, pH 9.15 (Gelman Scientific, Ann Arbor, Mich., High Resolution Buffer, Product #51104), and 3% (v/v) POLYBUFFER 96 (Pharmacia, Piscataway, N.J., product #17-0714-01). Electrophoresis was carried out for 90 min at 180 volts and 4° C. Gels were then overlaid with 1 ml of Corning C.ARDIOTRAK-CK reagent (Corning Catalog #470069), incubated for 37° C. for 20 min, and dried for 15 min at 60° C. Dried gels were scanned on a HELENA AUTO SCANNER and peak integration was performed manually using a HELENA QUICK QUANT III.

The results obtained are show in Table C.

TABLE C

| Time, hr | Conc. Change by Electrophoresis, % | | | Immunological Measurement | | |
|---|---|---|---|---|---|---|
| | MM$_{A'}$ | MM$_B$ | MM$_{(A+B)}$ | #19 | #9 | #19/ #9 × 100 |
| 0 | 100 | 0 | 100 | 100 | 100 | 100 |
| 1 | 79.4 | 20.6 | 100 | 100 | 100 | 100 |
| 2 | 73.8 | 26.2 | 100 | 100 | 100 | 100 |
| 3 | 68.8 | 31.2 | 100 | 100 | 100 | 100 |
| 4 | 56.4 | 43.6 | 100 | 53 | 100 | 53 |
| 14 | 24.1 | 47.0 | 71.1 | 19 | 79 | 24 |

This data shows that the test based on #9 antibody measure both CK-MM$_A$ and CK-MM$_B$. The test based on #19 antibody measures only CK-MM$_A$. The data also shows that the ratio of the amounts of native protein to the amounts of the analyte pair decreases as the native protein remains in contact with the endogenous conversion factors.

EXAMPLE 7

Suggested Diagnosis Using #9 Antibody

The following test results are given to show the clinical utility of measuring the analyte pair using the #9 antibody, using samples collected and frozen in February, 1987. Serial specimens were collected from patients suspected of having a myocardial infarction and tested with the immuoradiometric QUICK-MB assay described in U.S. Pat. No. 4,624,916 (International Immunoassay Laboratories, Inc. 1900 Wyatt Drive, Santa Clara, Calif. 95054. An electrophoresis method was used to detect LD abnormality Inversion of the ration of isoenzyme fractions 1 and 2 of LD was taken as the late indication of acute infarction. The transient increase in CK-MB above 3.3 EU/L is suggestive of acute myocardial infarction. The analyte pair (#9 antibody binding) concentration of 20% (=200 EU/L) is abnormal.

The procedure of Example 6 were followed with the exception that the rabbit antibody concentration is limiting.

TABLE D

| Patient ID | Time of Sample | CK-MB, EU/L | #9 Binding$^a$ |
|---|---|---|---|
| A$^{(b)}$ | 02/19/87 4 AM | 2.4 (nor.) | 87.8 (elev.) |
| | 02/20/87 4 AM | 20.4 | 63.5 |
| B$^{(c)}$ | 02/17/87 4 PM | >40.0 | 78.9 |
| | 02/17/87 11 PM | 31.0 | 48.9 |
| | 02/18/87 8 AM | 17.0 | 23.4 |
| | 02/18/87 6 PM | 8.6 | 32.6 (incr.) |
| | 02/21/87 9 PM | 2.6 (nor.) | 46.3 |
| | 02/22/87 Midnight | 2.9 | 24.0 |
| | 02/22/87 5 AM | 7.1 | 37.7 |
| | 02/22/87 4 PM | 10.4 | 25.9 |
| C$^{(d)}$ | 02/24/87 1 PM | 2.6 (nor.) | 23.9 (elev.) |
| | 02/24/87 5 PM | 12.7 | 34.9 |
| | 02/25/87 Midnight | 32.6 | 40.7 |
| | 02/25/87 5 AM | >40.0 | 56.9 |
| | 02/25/87 8 AM | >40.0 | 56.3 |
| | 02/25/87 11 AM | 10.0 | 72.7 |
| D$^{(e)}$ | 02/19/87 4 PM | 2.5 (nor.) | 32.6 (abnor) |
| | 02/20/87 1 AM | 3.2 (nor.) | 31.2 |

$^{(a)}$Analyte pair, % of highest calibrator, about equal to 1000 EU/L
$^{(b)}$Possible reinfarction detected earlier by #9 compared to CK-MB.
$^{(c)}$Patient undergoing reinfarction, detected earlier by #9 while CK-MB level is still descending.
$^{(d)}$Early detection by #9.
$^{(e)}$Patient had LD isoenzyme abnormatility (LD) flip, indicating delayed recognition of AMI. Sample normal by CK-MB measurement, abnormal by #9 analyte pair measurement.

EXAMPLE 8

Sandwich Immuoassay

The procedure of Example 6 is repeated with a limiting amount of immobilized primary antibody.

This sandwich immuoassay is designed for detection of recent infarction only. The amount of immobilized primary antibody, anti-CK-MM antibody, is limiting and designed to accommodate only low levels of CK-MM. In most patients, the level of total CK in the absence of a disease state is less than 230 IU/L at 37° C. During the early phase of the infarction, total CK increases. Because of the design as total CK increases, increasing amounts of it will remain in the liquid phase since the solid phase becomes saturated. The secondary antibody is $^{125}$I-labeled #9 antibody produced in accordance with the procedure of Example 4.

When the solid phase is capable of binding all CK-MM, there is no excess in the liquid phase, and all of the labeled, #9 antibody is available to bind the solid phase. As the level of Ck increases, increasing amounts of the labeled antibody will will remain in the liquid phase. This design gives a high level of bound activity only when the level of the analyte pair is high, and the level of total CK is low. The following results were obtained;

TABLE E

| CK-MM$_{(A + B)}$ % of highest calibrator | Bound Counts per min | | | | |
|---|---|---|---|---|---|
| | Total Activity, IU/L | | | | |
| | 62.5 | 125 | 250 | 500 | 1000 |
| 0 | 1556 | 1553 | 1695 | 1819 | 2708 |
| 20 | 7067 | 11920 | 18290 | 24800 | 23071 |
| 40 | 11673 | 18641 | 23275 | 22017 | 17651 |
| 50 | 13309 | 19802 | 23079 | 21330 | 15849 |
| 60 | 16339 | 21991 | 22774 | 20280 | |
| 80 | 18744 | 23242 | 22800 | 17802 | |
| 100 | 20824 | 23468 | 20974 | 16445 | |

As can be seen, the maximum counts per minute, at any given percent level of the analyte pair, occurs at a level of total CK. Any further rise in total CK would cause a decrease in counts.

We claim:

1. A method for determined the level of CK-MM$_A$ in a serum or plasma sample comprising interacting said sample with anti-(CK-MM$_A$) antibody, and determining the level of CK-MM$_A$ bound with anti-(CK-MM$_A$) antibody.

2. The method of claim 1 wherein the anti-(CK-MM$_A$) antibody is bound to an insoluble support, the insoluble support is contacted with said sample for a time sufficient to permit CK-MM$_A$ conjugation with anti-(CK-MM$_A$) antibody, and the amount of CK-MM$_A$ bound to the insoluble support is determined.

3. The method of claim 1 wherein an anti-(CK-MM) antibody is bound to an insoluble support, the insoluble support is contacted with said sample for a time sufficient to permit CK-MM$_A$ conjugation with the anti-(CK-MM) antibody, contacting the insoluble support with anti-(CK-MM$_A$) antibody, and determining the amount of anti-(CK-MM$_A$) antibody bound to the insoluble support.

4. The method of claim 1 wherein CK-MM$_A$ is bound to an insoluble support, the insoluble support is contacted with a mixture of said sample and labeled anti-(CK-MM$_A$) antibody for a time sufficient to permit CK-MM$_A$ conjugation with the anti-(CK-MM$_A$) antibody, and the amount of the label on the insoluble support or remaining in the mixture is determined.

5. A method for determining the level of CK-MM$_B$ in a serum or plasma sample comprising interacting said sample with anti-CK-MM$_B$) antibody, and determining the level of CK-MM$_B$ bound with anti-CK-MM$_B$) antibody.

6. The method of claim 5 wherein the anti-(CK-MM$_B$) antibody is bound to an insoluble support, the insoluble support is contacted with said sample for a time sufficient to permit CK-MM$_B$ conjugation with anti-(CK-MM$_B$) antibody, and the amount of CK-MM$_B$ bound to the insoluble support is determined.

7. The method of claim 5 wherein an anti-(CK-MM) antibody is bound to an insoluble support, the insoluble support is contacted with said sample for a time sufficient to permit CK-MM$_B$ conjugation with the anti-(CK-MM) antibody, contacting the insoluble support with anti-(CK-MM$_B$) antibody, and determining the amount of anti-($CK-MM_B$) antibody bound to the insoluble support.

8. The method of claim 5 wherein $CK-MM_B$ is bound to an insoluble support, the insoluble support is contacted with a mixture of said sample and labeled anti-($CK-MM_B$) antibody for a time sufficient to permit $CK-MM_B$ conjugation with the anti-($CK-MM_B$) antibody, and the amount of the label on the insoluble support or remaining in the mixture is determined.

9. A method for determining the level of $CK-MM_{(A+B)}$ in a serum or plasma sample comprising interacting said sample with anti-($CK-MM_{(A+B)}$) antibody, and determining the $CK-MM_{(A+B)}$ bound with anti-($CK-MM_{(A+B)}$) antibody.

10. The method of claim 9 wherein the anti-($CK-MM_{(A+B)}$) antibody is bound to an insoluble support, the insoluble support is contacted with said sample for a time sufficient to permit $CK-MM_{(A+B)}$ conjugation with anti-($CK-MM_{(A+B)}$) antibody, and the amount of $CK-MM_{(A+B)}$ bound to the insoluble support is determined.

11. The method of claim 9 wherein an anti-(CK-MM) antibody is bound to an insoluble support, the insoluble support is contacted with said serum sample for a time sufficient to permit $CK-MM_{(A+B)}$ conjugation with the anti-(CK-MM) antibody, contacting the insoluble support with anti-($CK-MM_{(A+B)}$) antibody, and determining the amount of anti-($CK-MM_{(A+B)}$) antibody bound to the insoluble support.

12. The method of claim 9 wherein $CK-MM_{(A+B)}$ is bound to an insoluble support, the insoluble support is contacted with a mixture of the serum sample and labeled anti-($CK-MM_{(A+B)}$) antibody for a time sufficient to permit $CK-MM_{(A+B)}$ conjugation with the anti-($CK-MM_{(A+B)}$) antibody, and the amount of the label on the insoluble support or remaining in the mixture is determined.

13. The method of claim 9 wherein the level of $CK-MM_A$ in said sample is determined by interacting said sample with anti-($CK-MM_A$) antibody, and determining the level $CK-MM_A$ bound with anti-($CK-MM_A$) antibody.

14. The method of claim 13 wherein the anti-($CK-MM_A$) antibody is bound to an insoluble support, the insoluble support is contacted with said sample for a time sufficient to permit $CK-MM_A$ conjugation with anti-($CK-MM_A$) antibody, and the amount of $CK-MM_A$ bound to the insoluble support is determined.

15. The method of claim 13 wherein an anti-(CK-MM) antibody is bound to an insoluble support, the insoluble support is contacted with said sample for a time sufficient to permit $CK-MM_A$ conjugation with the anti-(CK-MM) antibody, contacting the insoluble support with anti-($CK-MM_A$) antibody, and determining the amount of anti-($CK-MM_A$) antibody bound to the insoluble support.

16. The method of claim 13 wherein $CK-MM_A$ is bound to an insoluble support, the insoluble support is contacted with a mixture of said sample and labeled anti-($CK-MM_A$) antibody for a time sufficient to permit $CK-MM_A$ conjugation with the anti-($CK-MM_A$) antibody, and the amount of the label on the insoluble support or remaining in the mixture is determined.

17. An anti-($CK-MM_A$) antibody preparation which does not bind significantly with CK-MB, $CK-MM_B$ or $CK-MM_C$.

18. The anti-($CK-MM_A$) antibody of claim 17 covalently bonded to a label.

19. The anti-($CK-MM_A$) antibody of claim 17 covalently bonded to an insoluble support.

20. An anti-($CK-MM_B$) antibody preparation which does not bind significantly with CK-MB, $CK-MM_A$ or $CK-MM_C$.

21. The anti-($CK-MM_B$) antibody of Claim 20 covalently bonded to a label.

22. The anti-($CK-MM_B$) antibody of claim 20 covalently bonded to an insoluble support.

23. An anti-($CK-MM_{(A+B)}$) antibody preparation which binds with $CK-MM_A$ or $CK-MM_B$, but does not bind significantly with CK-MB, or $CK-MM_C$.

24. The anti-($CK-MM_{(A+B)}$) antibody of claim 23 covalently bonded to a label.

25. The anti-($CK-MM_{(A+B)}$) antibody of claim 23 covalently bonded to an insoluble support.

26. An assay kit containing an anti-($CK-MM_A$) antibody and an anti-($CK-MM_{(A+B)}$) antibody.

* * * * *